(12) United States Patent
Kosnitsky et al.

(10) Patent No.: US 8,483,354 B1
(45) Date of Patent: Jul. 9, 2013

(54) REDUCING IMAGING ARTIFACTS

(75) Inventors: Jason Kosnitsky, Framingham, MA (US); Alan Sliski, Lincoln, MA (US)

(73) Assignee: Orbital Therapy LLC, Bedford, MA (US)

( * ) Notice: Subject to any disclaimer, the term of this patent is extended or adjusted under 35 U.S.C. 154(b) by 0 days.

(21) Appl. No.: 13/035,983

(22) Filed: Feb. 27, 2011

Related U.S. Application Data

(60) Provisional application No. 61/308,738, filed on Feb. 26, 2010.

(51) Int. Cl.
*A61B 6/04* (2006.01)

(52) U.S. Cl.
USPC .......................................... 378/37; 600/407

(58) Field of Classification Search
USPC ............... 600/407–430; 378/84, 85, 145–159
See application file for complete search history.

(56) References Cited

U.S. PATENT DOCUMENTS

| 6,987,831 | B2 * | 1/2006 | Ning | 378/37 |
|---|---|---|---|---|
| 7,211,814 | B2 * | 5/2007 | Cadwalader et al. | 250/519.1 |
| 7,508,911 | B1 * | 3/2009 | Lee et al. | 378/84 |
| 7,697,660 | B2 * | 4/2010 | Ning | 378/37 |
| 7,742,566 | B2 * | 6/2010 | Hopkins et al. | 378/84 |
| 2004/0081273 | A1 * | 4/2004 | Ning | 378/37 |

* cited by examiner

*Primary Examiner* — Sanjay Cattungal
(74) *Attorney, Agent, or Firm* — Intrinsic Law Corp; Ibrahim M. Hallaj

(57) ABSTRACT

A patient support system for diagnostic and/or therapeutic radiologic procedures with geometric features that eliminate or reduce imaging artifacts created by the patient support is described. The artifact reducing features can be incorporated into an add-on patient positioning device, or directly within the standard diagnostic and/or therapeutic treatment table/couch. One possible configuration is to use a wave-like design of the portion of the patient support that remains in the radiation beam path where the anatomy to be imaged is located. Other configurations may include other geometric shapes or material distributions that serve the same purpose of eliminating artifacts in radiologic images.

18 Claims, 6 Drawing Sheets

REDUCING IMAGING ARTIFACTS

RELATED APPLICATIONS

The present application claims a benefit of the previously filed provisional application 61/308,739 assigned to Orbital Therapy. Some embodiments described herein are related to U.S. patent application Ser. Nos. 12/859,390 AND 12/815,812 all of which are herein incorporated by reference in their entirety.

SUMMARY

Various implementations of a positioning table for supporting a patient are described herein. The table can support the patient in a vicinity of a direct radiation beam. In some variations, the table can have an opening for positioning the first anatomy of the patient in contact with the direct radiation beam and a patient support component holding the second anatomy away from the direct radiation beam.

For example, the patient support component can have a beam entrance region, a multi-dense region and a beam exit region, such that the radiation beam enters the patient support component through the beam entrance region, passes through the multi-dense region and exits from the beam exit region, wherein the multi-dense region comprises a plurality of densities.

The beam entrance region and the beam exit region may or may not be specially configured. In some implementations they can simply refer to a surface of the multi-dense region. The multi-dense region can be shaped in a wave-like configuration. For example, the wave can include non-periodic variation of amplitude and spacing of the shape features in one, two or three dimensions.

The multi-dense region can be implemented using multiple material types. It can include one or more holes. The multi-dense region can have a form of a wave, configured such that the direct radiation beam does not travel along a prolonged straight line of any surface material.

In one variation, the positioning table can be configured to hold the patient in the prone position. In some variations, the multi-dense region can be implemented by placing a plurality of different materials along the path of the direct beam. In the case of a wave-like configuration, the wave can be implemented using different materials for each spike of the wave. The plurality of different materials can include at least two materials selected from the group of carbon fiber, composite, plastic, wood, metal. Other material types may also be suitable for the multi-dense region.

BACKGROUND

Prone breast diagnostic and treatment procedures are used to detect, biopsy and treat cancer. Today many procedures such as MRI (magnetic resonance imaging), CT (computed tomography), ultrasound and radiotherapy are performed with the patient in the prone position. This technique places the patient face down, allowing one or both breasts to be exposed below the patient for the particular procedure to take place. As patients vary in size, it can be important to have various interface platforms to accommodate the population, as well as have options for left breast, right breast or both at the same time. Although these modalities offer a non-invasive view of the human body, some artifacts can be present and distort the image. One type of image artifact that occurs in computed tomography happens when straight sections of support material are included in the imaging volume. The x-ray absorption along the straight line affects the x-ray spectrum and can generate a corresponding linear artifact in the resulting image during the reconstruction process. This artifact changes the Hounsfield number for the region within the artifact and can result in small errors in radiation treatment planning which use the Hounsfield number to estimate the absorption properties of the therapy beam. The goal of the device described is to reduce the artifacts introduced by the patient support surface by modifying the shape or material distribution of the patient support surface.

DETAILED DESCRIPTION

Figure 1:
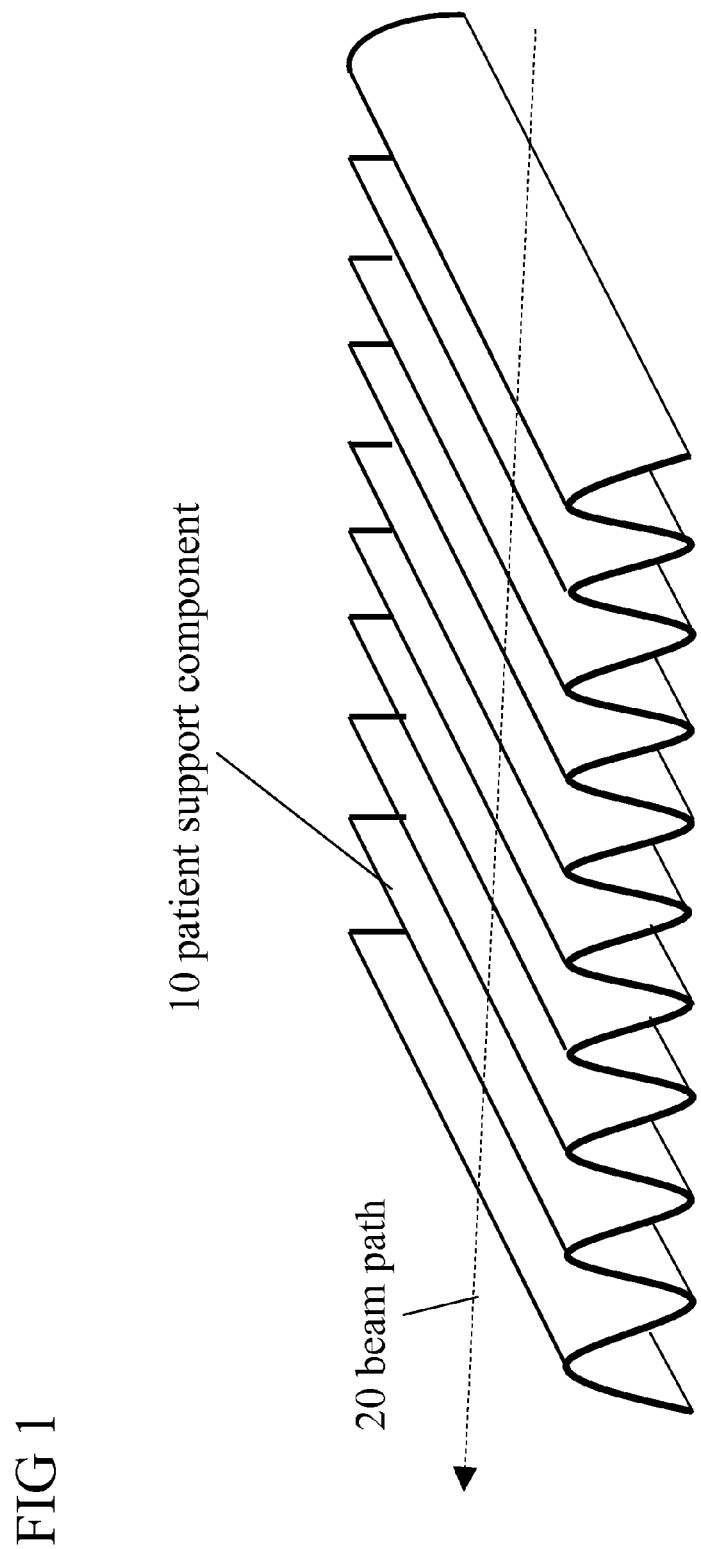
FIG. 1 is a perspective view of one possible design of the patient support component.

Patient imaging and treatment can be performed with the patient positioned in a number of ways, including supine (on the back) or prone (face down) positions. As an example, we will use CT-based breast imaging and subsequent radiation therapy to describe one possible application. Today, when it comes to radiotherapy most patients with breast cancer are still being imaged and treated in the supine position. Although some diagnostic imaging procedures such as biopsy and MRI can be done in the prone position, the radiotherapy departments typically perform CT scans (simulations) and treatment delivery in the supine position. Recently, there has been a trend to move from supine to prone as this increases the separation of the anatomy to be treated with radiation from critical structures within the patient and reduces target motion due to breathing.

When the patient undergoes a CT scan in the prone position to obtain the data required for treatment planning and delivery, an undesired shadow artifact can be present in the breast of interest if there are planar features in the patient support. This artifact can be caused by the typically planar structure of the patient support structure or table, which can be specifically designed for breast imaging and treatment.

In the case of breast cancer treatment, only one breast is treated and it needs to be isolated from the rest of the body in order to allow for direct, non-obstructed radiation beam access. The other breast as well as the patient are supported above the breast to be treated and are not in the way of the treatment beam. The observed image artifact is created by the planar support structure around the pendant breast that supports the patient. The planar surface which supports the patient at the level of the chest is in line with the x-ray beam during a CT scan and an artifact is created during the CT image reconstruction process which creates the appearance of a shadow within the breast of interest.

Most of these prone patient support structures are add-on devices that are placed directly on top of existing imaging and treatment tables, but in some cases they can be directly integrated into the imaging or treatment table. The undesired image artifacts can result in small errors in radiation treatment planning. For example, the artifact can influence the Hounsfield number used to estimate the absorption properties of the therapy beam. Devices and methods described herein can greatly reduce or eliminate the level of the artifact and, thus, improve the radiation treatment planning.

Multiple implementations of a patient support component are described. In one example, the patient support component can be used for prone breast radiotherapy and/or imaging. During the process of preparing a patient for prone breast radiotherapy, the patient is placed face down on top of the patient support table or device and imaged using a CT scanner. The breast of interest to be examined and/or treated is pendant below the patient support surface, and the other breast rests on the same relative plane as the rest of the body. In this case, at the time of CT simulation the surface supporting the patient can introduce an image artifact, which looks like a straight shadow cutting the image of the breast of interest. The appearance of the artifact (also referred to as the edge induced streaking) can resemble a shadow.

In one implementation, the described patient support component can reduce or eliminate the artifact by eliminating the planar geometry of the patient support in the region to be imaged. FIG. 1 demonstrates one possible design of the patient support component 10 where the radiation beam path direction 20 is indicated with an arrow. The patient support 10 may be of any non-linear shape and/or density variation, but one possible design is a wave-like configuration where the radiation beam path 20 does not travel along a prolonged straight line of the patient support component 10 resulting in the artifact projection. The patient support 10 can be made from any material such as carbon fiber, composite, plastic, wood, metal and the like. In some implementations, the patient support 10 can be implemented from a plurality of different materials, thereby creating a non-uniform density section for any given beam path. The wave form does not have to be uniform or of the same amplitude.

Figure 2:
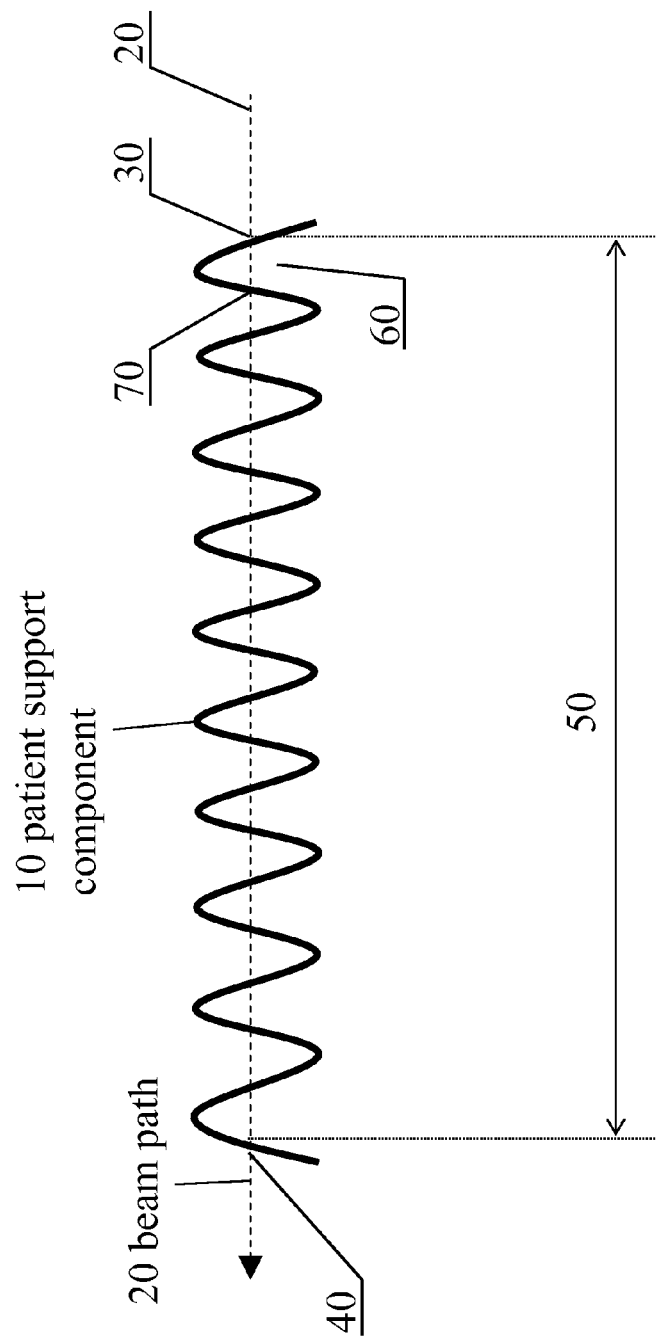
FIG. 2 is a side view of one possible design of the patient support component.

FIG. 2 shows the side view of the patient support component, where one possible design of the patient support 10 is placed along the radiation beam path 20. The patient support component 10 may be of any non-linear shape, but one possible design is a wave-like configuration where the radiation beam path 20 does not travel along a prolonged straight line of the patient support component 10 resulting in the artifact projection. The beam 20 enters the beam entrance region 30 and passes through the density of the material used to implement the patient support component 10. After the beam exits the material of the patient support component 10, it passes through a different density region 60. For example, the different density region can be made of air. After the different density region 60, the beam enters the material 70 of the patient support component 10 for a small interval. The lack of a long straight section of material reduces or eliminates the artifact seen in images of supports that incorporate long straight or planar elements. The patient support 20 can be made for any materials such as carbon fiber, composite, plastic, wood, metal and the like.

Figure 3:
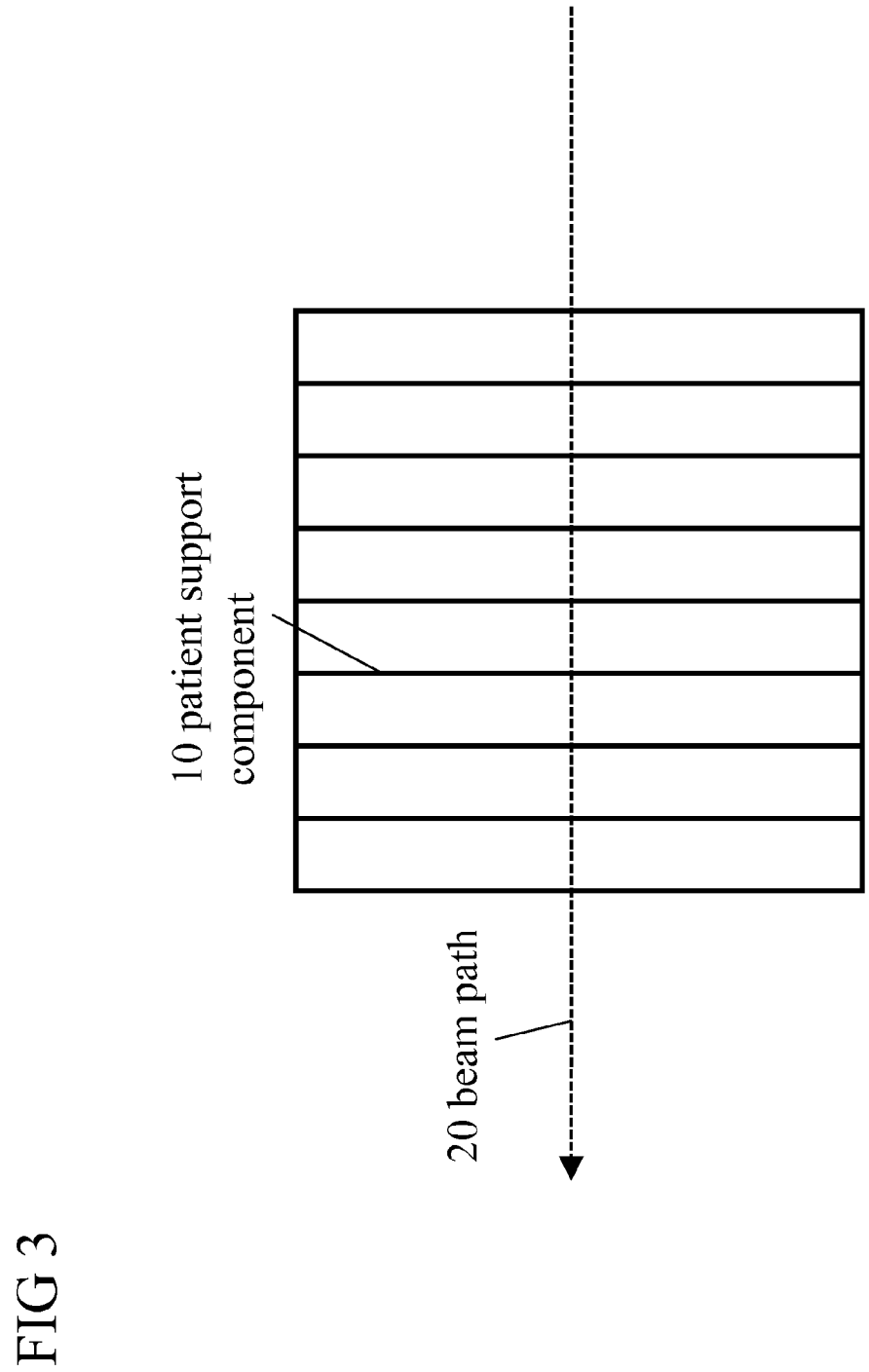
FIG. 3 is a top view of one possible design of the patient support component.

FIG. 3 shows the top view of the patient support component shown in FIG. 2

Figure 4:
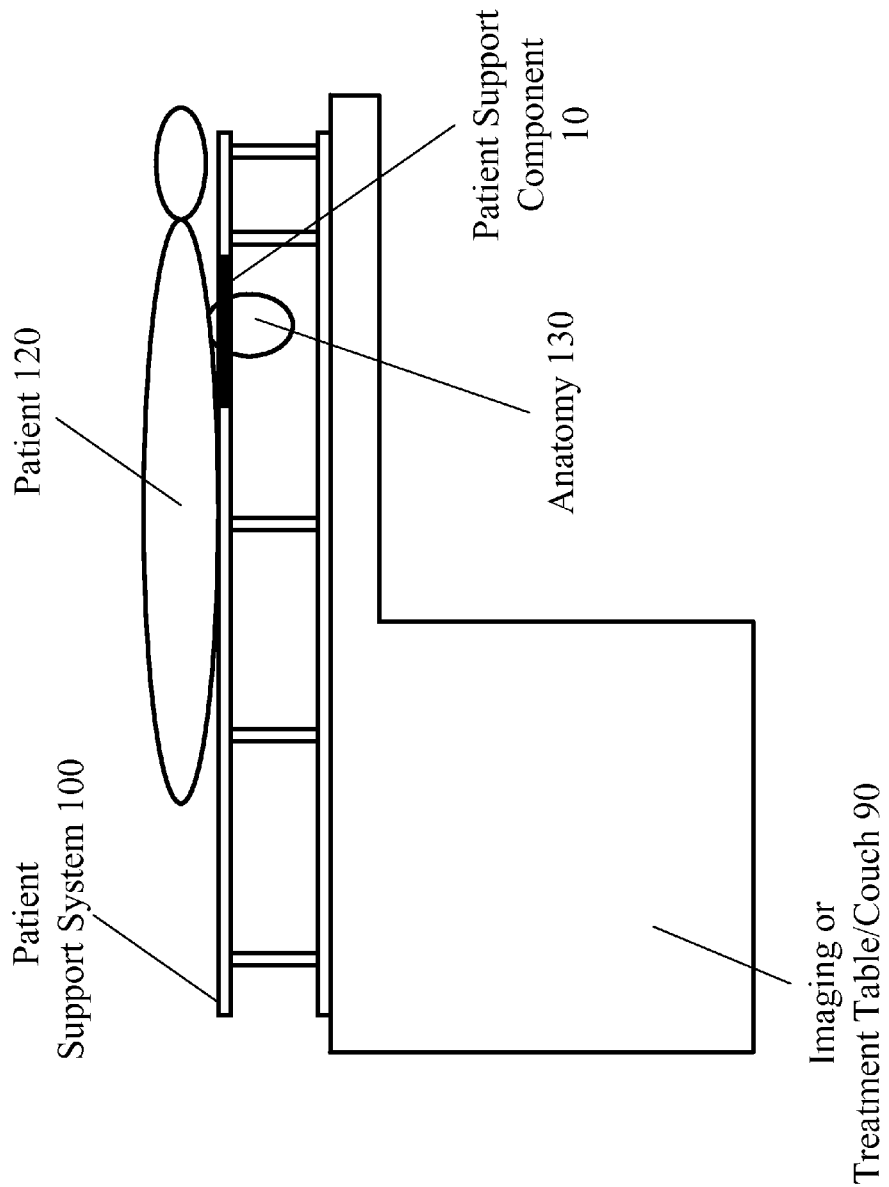
FIG. 4 demonstrates one possible use of the patient support component with an add-on prone breast positioning device.

FIG. 4 demonstrated one possible use of the patient support component 10 in conjunction with a patient support add-on system 100, which may be used with an imaging or treatment couch 90. In this example the patient 120 is placed on top of the patient support system 100, and the anatomy 130, in this case a breast is pendant below the patient support component 10.

Patient Support System 100 illustrates one example of a prone breast imaging and treatment platform used in radiation therapy and imaging. Some forms of the Patient Support System 100 are currently manufactured by Civco, Bionix, Orbital Therapy and others. In some implementations, the Patient Support system 100 comprises an upper surface, a lower surface and an aperture for the patient's anatomy. The lower surface of the Patient Support table can be further adapted for placement on imaging or treatment tables/couches. FIG. 4 also illustrates the Imaging or Treatment Table/Couch 90. The Imaging or Treatment Table/Couch 90 is a support structure that can be used to position the patient during medical procedures.

The patient support component 10 can be made from any material such as carbon fiber, composite, plastic, wood, metal and the like. In some implementations, the patient support 10 can be implemented from a plurality of the aforementioned materials.

Figure 5:
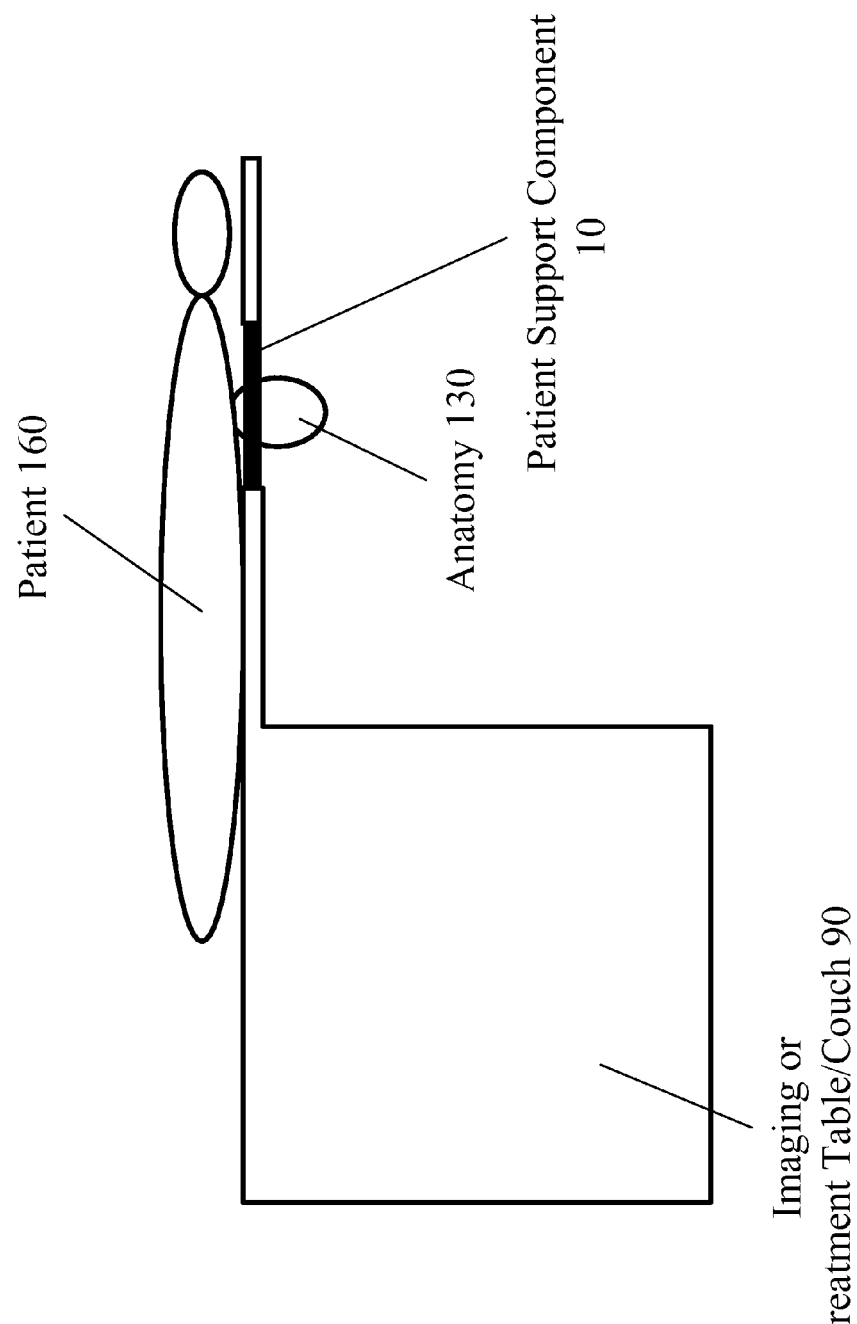
FIG. 5 demonstrated one possible use of the patient support component directly with an imaging, or treatment table.

FIG. 5 demonstrates one possible use of the patient support component 10 directly with the imaging or treatment couch 90. In this example the patient 120 is placed on top of the imaging or treatment table couch 90, and the anatomy 130, in this case a breast, is pendant below the patient support component 10.

Figure 6:
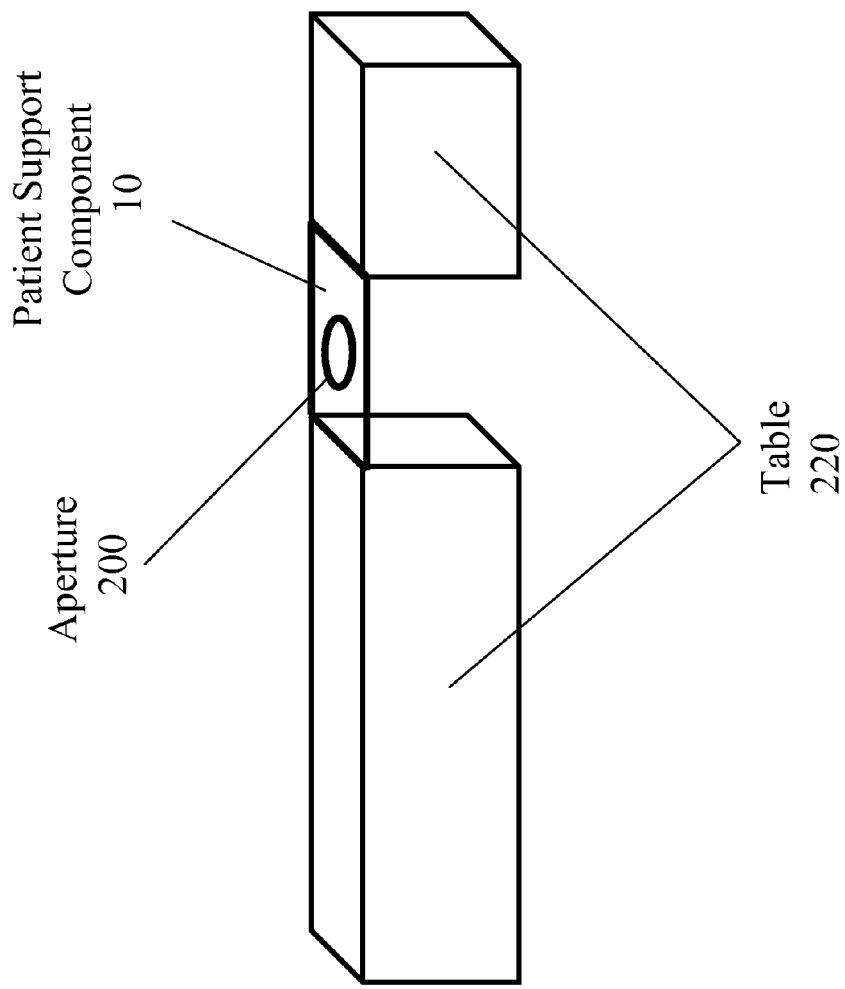
FIG. 6 demonstrates one possible use of the patient support component with a prone patient positioning table.

FIG. 6 demonstrates one possible use of the patient support component 10 with a prone position table 220, and an aperture 200 for anatomy of interest, such as breast, to pass through. The patient support component 10 can be made from any materials such as carbon fiber, composite, plastic, wood, metal and the like. In some implementations, the patient support component 10 can be implemented from a plurality of the aforementioned materials. In some implementation, the patient support component 10 can be placed on the top layer of the prone patient positioning table 220. The aperture 200 can be used to insert and position the anatomy of interest, such as breast, for medical imaging and/or treatment. The aperture 200 can be implemented within the patient support component. The aperture 200 can also be implemented adjacent to a side of the patient support component.

The invention claimed is:

1. A positioning table for supporting a patient, the patient having a first anatomy and a second anatomy, the table supporting the patient in a vicinity of a direct radiation beam, the table comprising:
    an opening for positioning the first anatomy in contact with the direct radiation beam;
    a patient support component holding the second anatomy away from the direct radiation beam;
    the patient support component having a beam entrance region, a multi-dense region and a beam exit region, such that the radiation beam enters the patient support component through the beam entrance region, passes through the multi-dense region and exits from the beam exit region, wherein the multi-dense region comprises a plurality of densities in a wave-like configuration of at least a portion of said multi-dense region.

2. The table of claim 1, wherein the wave-like configuration includes non-periodic variation of amplitude and spacing of the shape features in one, two or three dimensions.

3. The table of claim 1, wherein the multi-dense region is implemented using multiple material types.

4. The table of claim 1, wherein the multi-dense region includes one or more holes.

5. The table of claim 1, wherein the multi-dense region has a form of a wave, configured such that the direct radiation beam does not travel along a prolonged straight line of any surface material.

6. The positioning table of claim 1 configured to hold the patient in the prone position.

7. The table of claim 1, wherein the multi-dense region is implemented by placing the plurality of different materials along the path of the direct beam.

8. The table of claim 7, wherein the plurality of different materials includes at least two materials selected from the group of carbon fiber, composite, plastic wood, metal.

9. The table of claim 1, wherein the multi-dense region has a form of a wave, configured such that the direct radiation beam does not travel along a prolonged straight line of any surface material.

10. The table of claim 1, wherein the multi-dense region comprises a first density region and second density region, and the multi-dense region is configured such that the direct radiation beam passes through the first density region, followed by the second density region, followed by the first density region, followed by the second density region.

11. The table of claim 10, wherein the second density region is made of air.

12. A method for supporting a patient using a positioning table, the patient having a first anatomy and a second anatomy, the table supporting the patient in a vicinity of a direct radiation beam, the method comprising:
   positioning the first anatomy in contact with the direct radiation beam;
   holding the second anatomy away from the direct radiation beam by using a patient support component, the patient support component having a beam entrance region, a multi-dense region and beam exit region, such that the radiation beam enters the patient support component through the beam entrance region, passes through the multi-dense region and exits from the beam exit region, wherein the multi-dense region comprises a plurality of densities in a wave-like configuration of at least a portion of said multi-dense region.

13. The method of claim 12, wherein the wave-like configuration includes non-periodic variation of amplitude and spacing of the shape features in one, two or three dimensions.

14. The method of claim 12, wherein the multi-dense region is implemented using multiple material types.

15. The method of claim 12, wherein the multi-dense region includes one or more holes.

16. The positioning table of claim 12 configured to hold the patient in the prone position.

17. The method of claim 12, wherein the multi-dense region is implemented by placing the plurality of different materials along the path of the direct beam.

18. The method of claim 17, wherein the plurality of different materials includes at least two materials selected from the group of carbon fiber, composite, plastic, wood, metal.

* * * * *